United States Patent [19]

Charlier et al.

[11] Patent Number: 4,626,090

[45] Date of Patent: Dec. 2, 1986

[54] CUPOLA-TYPE OPHTHALMOLOGICAL APPARATUS THE VISUAL FIELD AND THE ELECTROPHYSIOLOGICAL EXAMINATION OF THE HUMAN EYE

[75] Inventors: Jacques Charlier; Bruno Buys; Jean-Pierre Sozanski; Yves Moschetto; Jean-Claude Hache; Pierre Francois, all of Lille, France

[73] Assignee: Institut National de la Sante et de la Recherche Medicale (Inserm), Lille, France

[21] Appl. No.: 600,479

[22] Filed: Apr. 16, 1984

Related U.S. Application Data

[63] Continuation-in-part of Ser. No. 218,773, Dec. 22, 1980, abandoned.

[30] Foreign Application Priority Data

Dec. 20, 1979 [FR] France .................................. 79 31887

[51] Int. Cl.[4] .............................................. A61B 3/02
[52] U.S. Cl. ................................................... 351/226
[58] Field of Search ........................ 351/224, 225, 226

[56] References Cited

U.S. PATENT DOCUMENTS

| | | |
|---|---|---|
| Re. 28,921 | 8/1976 | Haines et al. . |
| 2,441,031 | 5/1948 | Papritz . |
| 3,619,037 | 11/1971 | Pugh . |
| 3,951,527 | 4/1976 | Blanz ................................. 351/225 |
| 4,045,130 | 8/1977 | Krahn . |
| 4,255,023 | 3/1981 | House ................................ 351/226 |
| 4,260,227 | 4/1981 | Munnerlyn . |
| 4,310,224 | 1/1982 | Weilbach et al. . |

FOREIGN PATENT DOCUMENTS

484710 7/1952 Canada .
1132744 7/1962 Fed. Rep. of Germany .

Primary Examiner—Rodney B. Bovernick
Attorney, Agent, or Firm—Robert E. Burns; Emmanuel J. Lobato; Bruce L. Adams

[57] ABSTRACT

This invention relates to a cupola-type visual stimulation ophthalmological apparatus for examining the visual field of a patient and performing electrophysiological examinations. It comprises a projection screen consisting of the inner surface of a hemispherical cupola, the patient's eye being disposed centrally of the cupola during the examination. A device for projecting visual stimuli on the screen is provided in the upper portion of the cupola and comprises essentially a casing incorporating a light source, filter means, an object mask, a lens and a movable reflecting mirror located in the vicinity of the cupola center. This mirror is adapted to project toward any desired point of the screen a luminous stimulus perceived by the patient for measuring the extent of the patient's visual field. Moreover, with the projection device it is possible to illuminate the complete visual field according to criteria relating specifically to electrophysiological examinations. For this purpose, the casing comprises a window adapted to be masked for examining the visual field and to be opened for making electrophysiological examinations, the light rays from the light source being deflected through the window for illuminating the complete screen surface. The various optical control members necessary for performing visual tests can also be used for electrophysiological examinations since the projection device is polyvalent and thus capable of accomplishing both types of examinations.

14 Claims, 4 Drawing Figures

CUPOLA-TYPE OPHTHALMOLOGICAL APPARATUS THE VISUAL FIELD AND THE ELECTROPHYSIOLOGICAL EXAMINATION OF THE HUMAN EYE

BACKGROUND OF THE INVENTION

1. Field of the Invention

This invention is a Continuation In Part of the U.S. patent application Ser. No. 218,773 of Dec. 22, 1980, now abandoned. It relates to a cupola-type ophthalmological visual stimulation apparatus for examining the visual field and performing electro-physiological examinations of the human eye, during which the patient is subjected to various luminous excitations visible on a hemispheric screen.

1. The Prior Art

Apparatus for examining the visual field are already known, for example the apparatus described in the U.S. Pat. No. 4,045,130 to Krahn, which consists of a hemispheric projection screen receiving fixed luminous spots from a projector located in the upper portion of the cupola, or movable luminous spots from a complex apparatus disposed partly outside the cupola and comprising notably an articulated reversing lever adapted to project movable luminous stimuli on the concave surface of the cupola.

In its static version the stimulus projector consists of a bulb, a filter and a perforated mask, as well as a 90-degree reflector. The purpose of the perforations formed in the mask is to project the spots on the screen for measuring the patient's visual field. The more sophisticated version of the apparatus comprises a pivoted arm provided with optical reflectors whereby luminous stimuli can move on the screen for performing dynamic tests.

Another U.S. Pat. No. 2,441,031 discloses an ophthalmological apparatus for measuring the visual perimeter of a patient. According to this reference patent, the apparatus comprises a hemispherical screen on which a luminous spot is projected by a projector comprising notably a pivoted projection arm provided with reflecting mirrors. In parallel with the control of the pivoted projection arm, a path is formed on a diagram responsive to a mechanism coupled to the movable projector so as to trace the curve of the patient's visual perimeter.

It is worth pointing out that in the above-mentioned prior art constructions the device for projecting the movable stimulus extends partly outside the cupola and generally in front thereof.

Due to the type of design generally adopted for constructing apparatus of this type for examining the visual field of a patient, these apparatus are generally bulky and heavy.

However, progresses in the attempt to reduce the volume occupied by apparatus of this type have been achieved notably by using movable mirrors for example as disclosed in the U.S. Pat. No. 4,310,224 to Weilbach. However, the construction suggested by the Weilbach patent is attended by various inconveniences such as the use of a cumbersome power unit which must compulsorily be disposed at a distance from the movable reflecting mirror for clearing the space around this mirror. On the other hand, one of the mirror's movements is obtained by using a winch, thus limiting considerably the precision of the mirror's position. More particularly, servo means are contemplated for controlling the mirror.

It is also obvious that as a rule hitherto known projection apparatus for the dynamic examination of the visual field of the human eye comprise a movable reflection mirror having only one degree of liberty. In fact, the use of a hemispheric screen requires that the mirror be driven with a very particular movement for simulating a rectilinear movement of the luminous spot in the various portions of the hemisphere. To avoid the complicated means necessary for obtaining this very particular movement, hitherto known devices such as the one disclosed in the U.S. Pat. No. 4,260,227 to Munnerlyn utilize a mirror having an axis of rotation and capable on the other hand to move along the edge of the hemispheric screen.

In the present state of the art electro-physiological examinations are accomplished by using apparatus completely separate from the apparatus described hereinabove for examining the visual field.

SUMMARY OF THE INVENTION

Various diagnosis methods utilized by ophthalmologists consist in estimating the manner in which the patient's visual organs process the data received by the retina. The visual system is thus regarded as a "black box" receiving at its input data in the form of "visual stimuli" and delivering "responses" at its output.

It is possible for example to utilize either the voluntary response of the patient who depresses a knob when he perceives a stimulus, or electrical activities caused by visual stimuli and received either from the retina "ERG=electroretinogram", or from the visual cortex "VEP=visual evoked potential".

A pathological attack of the structures of the visual system is attended by characteristic changes in the responses obtained in the presence of specific visual stimuli. These diagnosis methods are at the same time overrunning, relatively cheap and extremely rich from the semiological point of view for they are applicable to a wide range of pathologies of the visual system, whether the retina, the optical nerve or the cortical centres are concerned. These various examinations require the generation of specific visual tests of which the light distribution in both space and time is determined with a sufficient degree of precision.

For a long time apparatus for projecting data on a cupola-shaped screen have been used for visual field examinations.

The use of a cupola is advantageous because the patient is placed in a well-controlled visual environnement, the integrating properties of the sphere permitting of obtaining a uniform luminous surrounding as required for determining the degree of luminous adaptation of the retinian receptors (cones and rods).

On this cupola-shaped screen tests are presented of which the brightness, the position and also the size, the projection time and the color can be modified at will.

The visual field examination proper consists in detecting and valuating, for a motionless eye, changes in the luminance threshold perceived in various position in space.

Cupola screens have also been used of late for performing visual electro-physiological examinations, notably for retina examinations. Reference may be made to the article entitled "A standardizable method for separating rod and cone responses in clinical electroretinography" by J. R. Brunette, American Journal of Ophthalmology 1973, 1975, 863-845, and to the article entitled "A Ganzfeld stimulator for electroretinography", by Gunkel R.; Bergsmand, Gouras P., Archives Ophthalmomogy 1976, 94, 669-670.

In this field the primary advantage offered by the use of a cupola is to permit a uniform retina stimulation.

In fact, the electrical responses of the retina is dependent upon the luminous intensity of the stimulus. To obtain a uniform, easily interpretable response, it is of primary importance that each element of the retina receives nearly the same amount of light. Now this requirement is obviously not met with conventional stimulators utilizing a short-reach flash source, for in this case only the central area of the retina is illuminated directly, the peripheral area receiving a diffused light of reduced intensity.

The various problems discussed hereinabove are solved by using a cupola capable of illuminating uniformly the complete retina surface. On the other hand, with a cupola it is possible to control with precision the level of luminous adaptation of the retina and to estimate under ideal conditions the capacity of the visual system to adapt itself to dark luminous environments (for example in AERG and EOG electroretinographic adaptation examinations).

Apparatus of this type are now available and have substantially similar designs. In addition to the cupola, they comprise a flash-type light source of which the luminance, color and ON time are easily adjustable.

It is the essential object of the present invention to provide an ophthalmological apparatus for the visual stimulation of the patient's retina in a cupola, which permits of examining the visual field and making electro-physiological examinations.

Therefore, the present invention affords a substantial reduction in the cost of equipments for ophthalmologists' consulting rooms, the practitioners having thus a single apparatus at their disposal for accomplishing the two types of examinations.

Stress may be laid on the fact that a number of functions are common to both types of apparatus, namely the cupola shaped screen, the environment illumination, the systems for controlling the luminance, color and ON-time of the stimulation, the examination data control systems and also the dialogue with the physician. Consequently, the combined performance of the two types of examinations does not require an important multiplication of the equipment. On the other hand, from the medical point of view, the possibility of performing visual-field and electrophysiological examinations under strictly identical conditions is obviously advantageous. These examinations are not competitive with each other and in many instances they are complementary since the data obtained are of different characters. However, it is interesting to compare the results and in this case the use of identical examination conditions is particularly advantageous.

Besides, the use of multi-function instruments reduces the space occupied in the ophthalmologist consultation room by the examination equipment.

Furthermore, the present invention is also directed to a device for driving the movable mirror for reflecting the luminous stimulus during a visual field examination, this improved device having particularly reduced overall dimensions. The mirror driving mechanism according to the present invention is advantageous in that the complete projection device can be installed in the cupola above the patient's head. With this original arrangement the overall dimensions of the apparatus are reduced appreciably and on the other hand since the mirror driving mechanism is disposed in close vicinity of the mirror the moving masses are reduced accordingly, a feature advantageous from the dual point of view of dynamics and accuracy.

The invention will now be described more in detail with reference to the accompanying drawings.

DESCRIPTION OF THE PREFERRED EMBODIMENT

The present invention relates to an improved cupola-type ophthalmological visual stimulation apparatus for examining the visual field of a patient and performing electrophysiological examinations.

Figure 1:
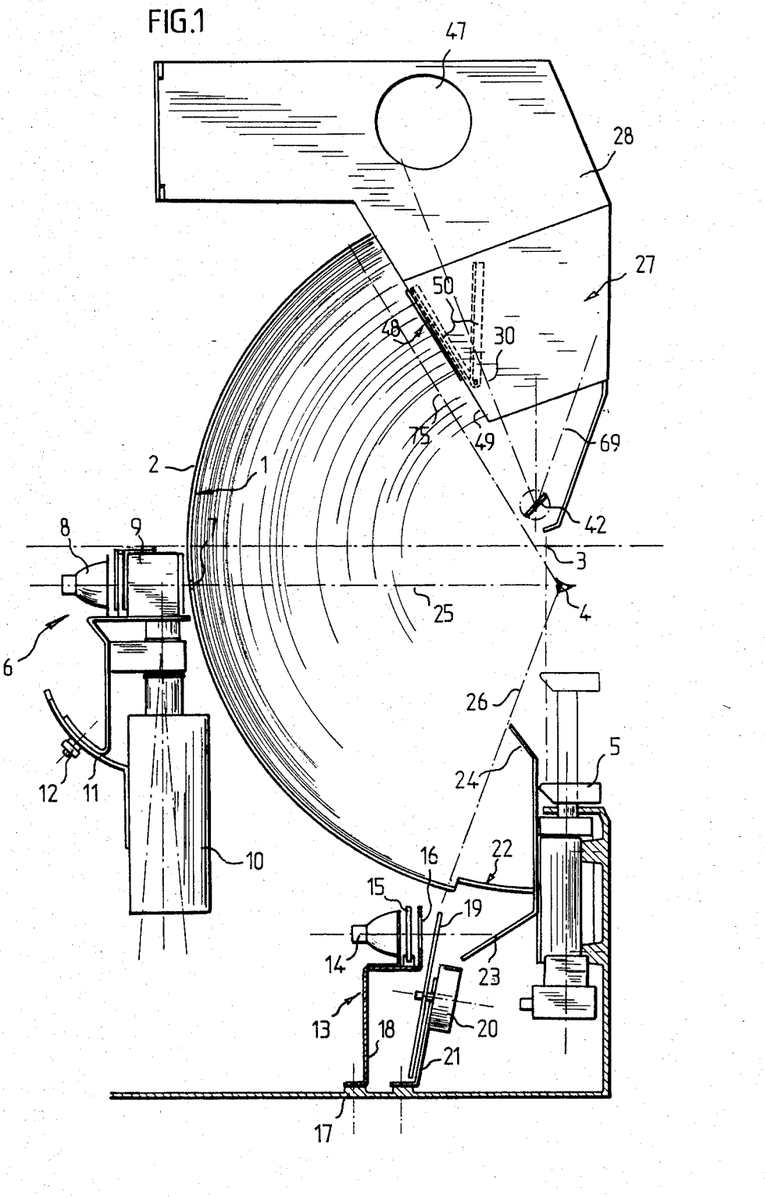
FIG. 1 illustrates diagrammatically in axial cross-sectional view the ophthalmological apparatus for visual stimulation according to the present invention.

Referring firstly to FIG. 1 of the drawings, the ophthalmological apparatus according to the present invention comprises essentially a screen 1 formed on the inner surface of a hemispherical cupola 2 having a centre 3 as shown in FIG. 1.

The patient's head (not shown in FIG. 1) is normally so positioned that the eye to be examined is located close to the centre 3 of the cupola. In the specific and preferred form of embodiment shown in FIG. 1, the patient's eye 4 is slightly recessed from the centre 3 of the cupola and at a level slightly inferior thereto. In the example illustrated, the amount of recess is of the order of 10 mm and the difference in level is about 39 mm.

From a purely optical point of view, it is preferred that the patient's eye 4 be positioned as close as possible to the centre 3 of the cupola; however, a compromise must be sought because the centre 3 of cupola 2 is also the optimal locus of the reflection mirror of the projection apparatus to be described in detail presently.

Throughout the examination the patient's head is held in a fixed position notably by using a chin-rest 5 adjustable both vertically and horizontally so that it can be adapted to any head size and used for examining the left eye and the right eye separately.

Considering the fact that notably for measuring the visual field of the patient it is of primary importance that the eye be kept in a fixed position during the test, the ophthalmological apparatus according to the present invention comprises a device 6 for checking the position of the patient's eye. This device 6 comprises suitable and known means for controlling through an orifice 7 formed in the cupola 2 the position of the patient's eye during the test.

The position control device 6 comprises a source 8 of infrared radiation disposed behind the cupola-shaped screen 2, condensers and filters housed in a casing 9, for illuminating the patient's eye with infrared light not perceived by the patient and consequently without causing any discomfort to the patient during the test. With the assistance of a semi-reflecting device also disposed within the casing 9 a "vidicon" type tube 10 permits of observing and localizing the patient's eye 4 illuminated by the source 8 of infrared radiation.

The video tube 10 is mounted on the frame structure of the ophthalmological apparatus by means of a curved sliding lug 11.

For performing certain types of visual examinations or tests, the screen 1 must be illuminated uniformly. For this purpose, the ophthalmological apparatus according to the present invention comprises in its lower portion a device 13 for uniformly illuminating the screen 1.

According to the preferred form of embodiment of the invention shown in FIG. 1, the device for uniformly illuminating the screen 1 comprises a light source 14 followed by a heat shield 15 and a diaphragm 16. This assembly is mounted on the frame structure 17 of the ophthalmological apparatus with the interposition of a mounting plate or bracket 18.

In addition, atténuator filters 19 may be disposed across the path of the light beams emitted by the source 14 so as to illuminate the screen 1 of the ophthalmological apparatus Wth different light levels. The filters 19 consist preferably of sectors disposed on the periphery of a disc mounted on the output shaft of a remote-controlled step-by-step motor 20 so that by properly rotating the disc the selected filter can be brought to its operative position with respect to the source 14. The motor 20 is mounted on the frame 17 of the apparatus by means of another plate or bracket 21.

The uniform lighting unit device 13 is disposed externally of the cupola 2 at the lower portion of the ophthalmological apparatus and the light rays emitted from the lighting device 13 are introduced into the cupola 2 through a notch 22 of said lower portion and reflected into the cupola 2 by a diffusing screen 23 struck by the light beam emitted from the light source 14.

A second diffusing screen 24 is disposed internally of the cupola 2 substantially vertically above the notch 22 for reflecting one fraction of the rays penetrating into the cupola 2 through said notch 22 towards the lower portion of the hemispherical screen 1. Thus, all the inner surface of the screen 1 is illuminated uniformly as necessary for performing certain visual tests.

For accomplishing such tests under the best possible condition it is definitely necessary that the patient be prevented from seeing in his visual field the projection means disposed about the screen. If 25 denotes the axis from the orifice 7 for checking the fixing of the patient's eye 4, it is required that the screen 24 and the notch 22 be located externally of the lower limit of the visual field shown in FIG. 1 in the form of an axis 26 set at an angle of about 70 degrees to said axis 25.

Figure 2:
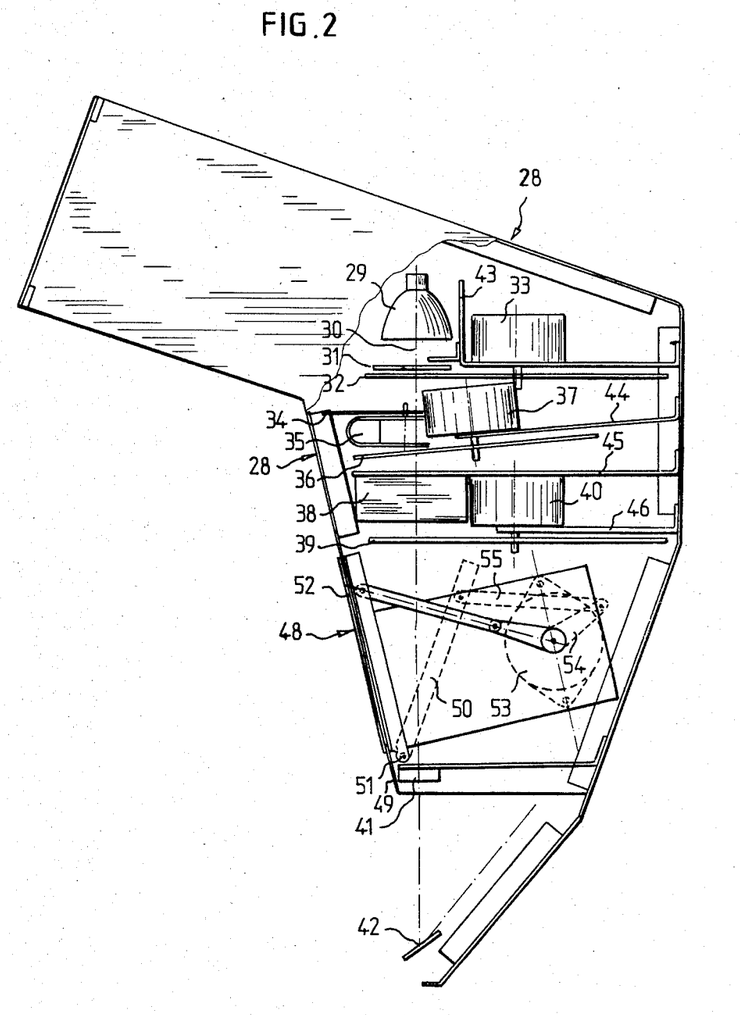
FIG. 2 is another section showing the projection device with its internal component elements.

It will also be seen in FIG. 1 that a projection device 27 is arranged in the upper portion of cupola 2. This device, shown more in detail in FIG. 2, is plumb to the patient's head. For the same reasons as those given hereinabove the projection device 27 must be located outside the visual field of the patient. Reference numeral 28 designates the axis at the upper limit of the patient's visual field. It will be seen that in the preferred form of embodiment of the present invention this axis 28 is set at an angle of about 60 degrees to the horizontal axis 25. The projection device 27 is located beyond this upper limit 28 of the visual field.

According to the present invention, the projection device is adaped to display on screen 1 either a movable stimulus for examining the visual field or a "global stimulation" for performing electrophysiological examinations. The use of a projection device capable of performing the two above-mentioned functions is particularly advantageous since it converts the ophthalmological apparatus of the present invention into a polyvalent apparatus.

By its specific design, the ophthalmological apparatus according to the present invention is particularly compact since, by way of example, satisfactory results have been obtained with a cupola having an inner radius of 330 mm.

FIG. 2 illustrates the preferred form of embodiment of the projection device 27 of the present invention.

This projection device 27 comprises a casing 28a so constructed as to prevent notably any external diffusion of light.

This casing 28A encloses a light source 29 for example of a halogen type.

The light rays generated by the source 29 are directed along an optical axis 30 through a thermal filter 31.

Beyond this thermal filter 31 the light rays pass through a color filter 32 disposed preferably on a sector of a disc carrying on its periphery a complete range of filters as in the case of the uniform lighting device described in the foregoing. This filter holding disc 32 is rigid with the output shaft of a controlled motor 33 adapted to position the filter consistent with the test to be performed across the path of the light beam emitted from the source 29.

In the preferred form of embodiment illustrated in FIG. 2 the projection device 27 also comprises a motor-driven shutter 34 consisting for example of a disc having suitable notches cut in its outer periphery and driven by a motor 35. The motor-driven shutter disc 34 is thus adapted to "hatch" the light rays at a frequency proportional to the rotational speed of motor 35. An attenuator filter in the form of a disc 36 is also interposed in the path of the light rays on the output side of the motor-driven shutter 34. This disc-shaped attenuator filter 36 is also mounted to the output shaft of another motor 37 so controlled as to position the filter providing the desired attenuation across the path of the light rays.

A diffusing filter 38 is also disposed in the path of the light beam for imparting the desired uniformity to the light rays emitted from the source 29. Another disc 39 constituting an object carrier is disposed on the output side of the diffusing filter 38 so that the desired images can be projected on the screen. This object-carrying disc 39 is controlled by a motor 40 so that, according to the test to be performed, the image best suited for the purpose can be projected. A lens 41 is also provided for focusing the image projected on the screen.

The light rays are then reflected on a movable mirror 42 which, by virtue of its mobility, can project the light stimulus on any desired point of the screen. The mechanical device for monitoring the mirror 42 with two degrees of liberty will be described more in detail presently.

According to the specific mechanical construction contemplated for the projection device 27, the light source 29 is secured to the casing 28 by means of a bracket 43 supporting at the same time the motor 33 for rotatably driving the color filter 32 and the thermal filter 31. Another plate 44 secured to the casing 28 supports the motors 35 and 37 driving the power shutter 34 and the attenuator filter 36, respectively. A further plate 45 secured to the casing 28 supports the diffusing filter 38.

The assembly also comprises a plate 46 parallel to plate 45 for holding in position the motor 40 driving the object carrying disc 39.

An opening 47 (FIG. 1) is provided for dissipating the heat generated by the light source 29. This opening 47 is formed laterally on the casing 28 and externally of the cupola 2 to prevent any ingress of stray light rays into the concave test screen 1.

The projection device 27 described hereinabove permits of displaying stimuli on the screen 1 in a manner fully adapted to the examination of the patient's visual field.

In order to enable different types of examinations to be made, the light source 29 and the various filters are selected to suit perimetry tests under photopic conditions with an illumination from 1 to 1,000 lux, as well as mesopic perimetry tests with an illumination of 0.01 to 10 lux, scotopic perimetry tests and the measurement of the curve of adaptation to darkness under an illumination of $10^{-7}$ to $10^{-3}$ lux.

According to the present invention, the projection device 27 is characterized in that it is also adapted for performing electrophysiological examinations.

For this purpose, the casing 28 of projection device 27 comprises a window 48 cut in the casing wall 49 which faces the screen 1 when the projection device 27 is positioned at the upper level of the cupola 2 as shown in FIG. 1. This window 48 can be closed for accomplishing visual field examinations as described in the foregoing, for which it is essential that no stray light ray can filter through the window 48.

In contrast, when electrophysiological examinations are to be made, the window 48 is cleared to provide an opening facing the screen 1. Moreover, reflecting means 50 are fitted across the path of the light rays emitted from the source 29 for deflecting said light rays through said window 48 toward the screen 1 within the cupola 2.

Thus, the optical apparatus, namely the light source 29, the thermal filter 31, the colored filter disc 32, the power shutter 34, the attenuator filter disc 36, the diffusing filter 38 and the object-supporting disc 39 may again be used for performing electrophysiological examinations.

Preferably, the reflecting means 50 consist of a white mat diffusing screen. This feature is important for obtaining a uniform illumination of the screen 1.

This diffusing screen 50, according to a preferred form of embodiment of the invention, is rotatably mounted on the casing 28 about a pivot axis 51 disposed along one edge of window 48. With this arrangement it is possible to either fold down the screen 50 against the window 48 for masking this window during visual field examinations, or on the contrary, by simply pivoting the screen as shown in dash lines in FIG. 2, clearing the opening of window 48 and interposing an obstacle in the path of the light rays shown diagrammatically by the optical axis 30 so as to deflect said rays through the window 48 toward the screen 1.

A Fresnel lens 52 is advantageously provided on the casing 28 of projection device 27 across the window aperture 48 for improving the uniformity of illumination of the screen 1. In fact, as a consequence of the upper position of the projection device 27, most of the light rays must be deflected toward the lower portion of screen 1 which is the remotest area from the projection device 27.

The rotation of the diffusing screen 50 is controlled by means of another motor 53 provided on its output shaft with an arm 54 pivotally connected to one end of a rod 55 having its opposite end pivotally connected in turn to the diffusing screen 50. Therefore, the simple rotation of motor 53 is attended by the rotation of arm 54 causing the reciprocating movement of rod 55 and consequently the angular movement of diffusing screen 50.

From the foregoing it will be readily understood that the projection device of this invention is particularly compact. In fact, the complete projection device can be concentrated both optically and mechanically into an area just overlying the patient's head within the limits of the cupola 2.

Figure 3:
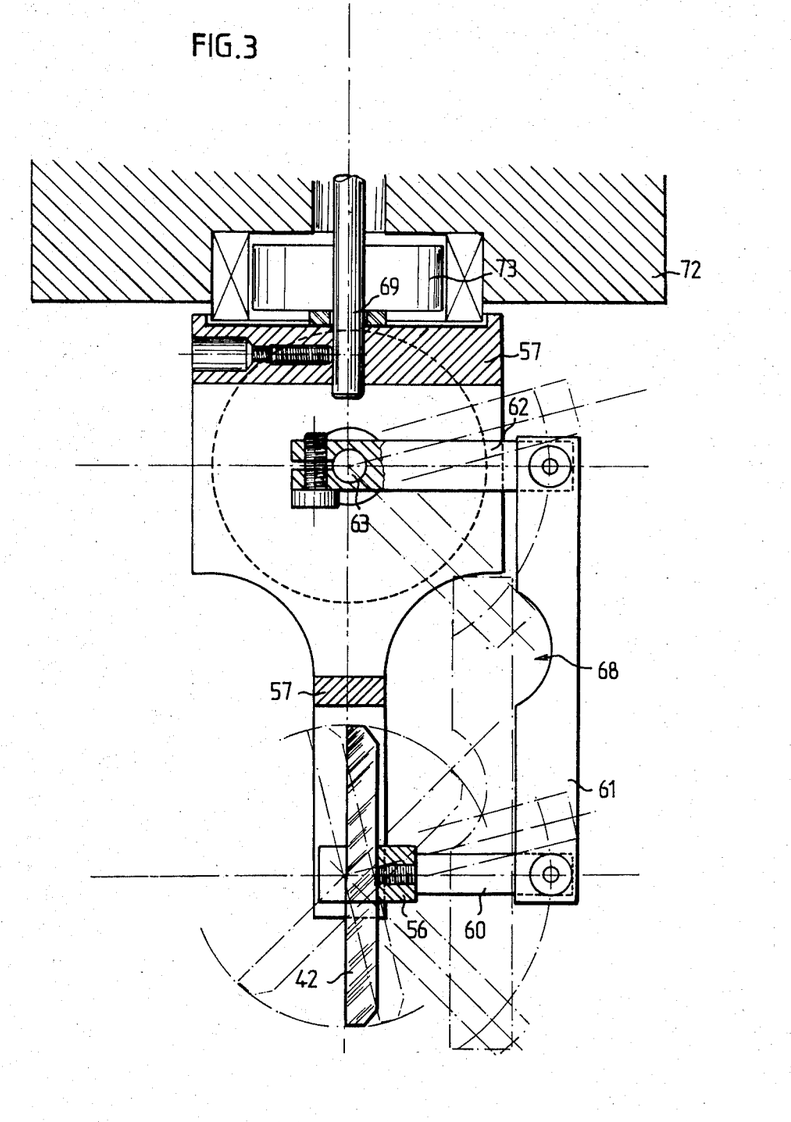
FIG. 3 is a sectional and side-elevational view of the driving mechanism for the movable reflection mirror, according to a preferred form of embodiment thereof.
Figure 4:
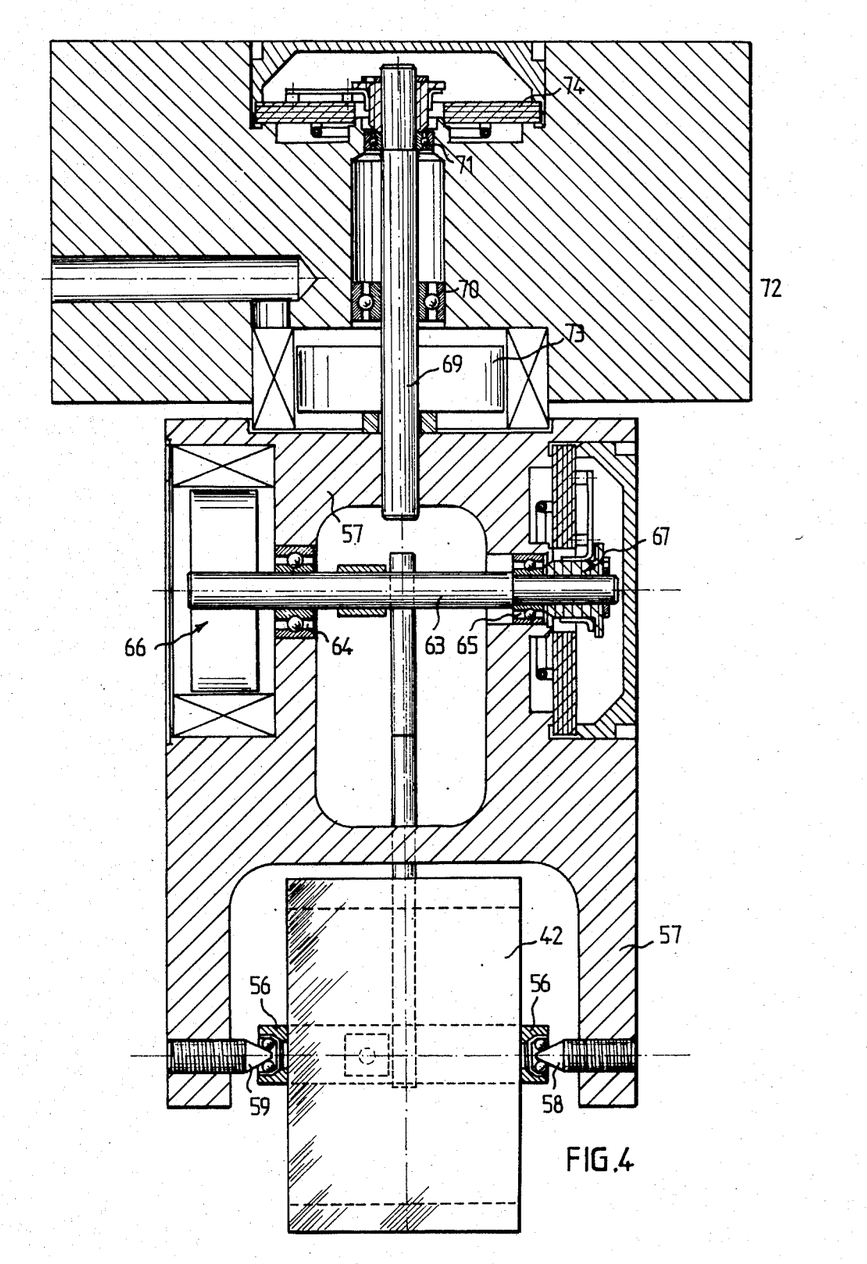
FIG. 4 is a front elevational and sectional view of the mechanism for driving the movable mirror of FIG. 3.

The mechanism controlling the movements of the movable mirror 42 is illustrated in details in FIGS. 3 and 4 of the drawings. The specific design shown in these Figures is also advantageous in that it permits of combining two essential features as required in mechanisms of this type for adapting them to the projection of luminous stimuli on the screen 1, that is, reduced overall dimensions in order to obtain a satisfactory kinetic operation and a position of the patient's head in close vicinity of the centre 3 of the cupola for obvious geometrical reasons. On the other hand, the control mechanism must be so designed that its position can be controlled with a high degree of precision, this optimum position permitting of defining the limits of the patient's visual field.

In the preferred form of embodiment of the invention shown in FIG. 1, the mirror 42 is located substantially symmetrically in relation to the centre 3 of the cupola and to the patient's optical axis 4.

This mirror 42 is fixed centrally of a strap 56 for example by cementing. This strap 56 is rotatably mounted in a frame structure 57 by means of a pair of ball-bearing type pivot pins 58 and 59. With this arrangement, the mirror can pivot in a vertical plane.

The movements of strap 56 are controlled by means of a lever 60 secured to the rear portion of strap 56, this lever 60 being pivotally connected to a rod 61 pivoted in turn to another lever 62 as shown in FIG. 3. This second lever 62 is rotatably rigid with a pivot pin 63 mounted in ball-bearings 64 and 65 reacting against the upper portion of the frame structure 57.

This shaft 63 comprises at one end a driving torque motor 66 and at its other end an angular pickup 67 for controlling the position of mirror 42.

The rod 61 has formed in its central portion a notch 68 engageable by the upper portion of mirror 42 when the latter is strongly inclined.

With the above-described arrangement the mirror is movable with one degree of liberty.

A second degree of liberty is obtained by rotatably mounting the frame 57 on a pivot shaft 69 and in ball-bearings 70 and 71 for connecting the mirror positioning mechanism to the frame structure 72. The pivot shaft 69 is controlled by means of a torque motor 73 located in the lower portion of pivot shaft 69 as shown in FIG. 4, and its position is controlled by means of a position sensor 74 disposed on the upper portion of shaft 69.

In the preferred form of embodiment described hereinabove the axis of shaft 69 is inclined by 20 degrees to the vertical, as shown in FIG. 1, and the optical axis 30 is also inclined by 20 degrees to the vertical symmetrical to said axis of shaft 69.

The function of mirror 42 is to permit the shifting of the stimulus within the entire visual field of the patient, i.e. with reference to the fixation point aimed by the patient's eye, up to 60 degrees in the upper portion, 70 degrees in the lower portion, 60 degrees on the temporal side and 95 degrees on the nasal side of screen 1.

As clearly apparent from the above-mentioned data, the extent of the visual field of a patient is not symmetrical with respect to the fixation point.

To reduce the dimensions of screen 1, and according to a specific feature characterizing the present invention, two fixation points, namely for examining the visual field of the right eye and the visual field of the left eye of the patient, are taken. These fixation points are located on the horizontal on either side of the orifice 7 for controlling the fixation of the patient's eye.

The angular shift of the fixation points of the left eye and right eye in relation to the control orifice 7 is equal to 15 degrees.

The left eye fixation point is shifted to the right in relation to the fixation control orifice 7 and the right eye fixation point is shifted to the left in relation to the fixation control orifice 7.

With this arrangement it is possible to use a single fixed orifice 7 for controlling the fixation, and moreover this orifice 7, in the case of the left eye and right eye examination, is coincident with the blind spot of the patient and therefore not perceived by the patient.

Moreover, the angular shifting of the fixation points permits of reducing appreciably the dimensions of the screen 1.

Since the extent of the visual field is about 95 degrees on the temporal side and about 60 degrees on the nasal side, during the examination of, for example, the right eye, the patient fixes with this eye the fixation point located 15 degrees to the left of the central orifice 7 for controlling the fixation. Consequently, the extent of the explored field with respect to this central orifice 7 for controlling the fixation is 95−15=80 degrees on the temporal side and 60+15=75 degrees on the nasal side.

To cover the complete visual field, the screen must therefore reach 80 degrees on either side of the central orifice 7 for controlling the fixation when examining the right eye and the left eye.

By virtue of this arrangement of screen 1 it is thus possible to reduce its overall dimensions and consequently to simplify its installation in a hospital room. The fixation points are advantageously obtained by projecting a light beam through the cupola. In this case red electroluminescent diodes are used which are energized in any known and suitable manner. The purpose of this arrangement is to make the fixation points invisible to the patient when they are OFF.

Of course, other forms of embodiment may occur to those conversant with the art without departing however from the basic principles of the invention as set forth in the appended claims.

What is claimed as new is:

1. Apparatus for examining the field of vision of a patient, comprising a dome of hemispherical shape provided on its inner surface with a screen having a central fixation point, means for positioning the head of a patient with his eye just below the center of said dome and directed toward said fixation point, unitary means for illuminating said screen and projecting a movable stimulating image on said screen, said unitary illuminating and projecting means comprising a casing, a light source in said casing, a small mirror located below said light source and just above the center of said dome, optical means for transmitting a beam of light along an optical axis from said light source to said mirror, said optical means comprising a condensing lens, variable filter means, image producing means and a focusing lens for projecting an image on said mirror for reflection by said mirror onto said screen, means for mounting said mirror for rotation about first and second axes perpendicular to one another, first motor means for selectively rotating said mirror about said first axis and second motor means for selectively rotating said mirror about said second axis to produce movement of said image on said screen, a window aperture cut in a wall of said casing between said light source and said mirror, light-reflecting means hingedly mounted at a lower side of said window aperture for movement between a first position in which it closes said window aperture and a second position in which it intercepts the transmission of light from said light source to said mirror and directs light from said light source out through said window aperature to illuminate said screen, said entire unitary illuminating and projecting means including said casing, said light source, mirror, lens, filter means, image producing means, and mirror mounting and rotating means, being disposed within a space immediately above the patient's head and just beyond the upper limit of the patient's field of vision.

2. The apparatus of claim 1 wherein said light-reflecting means comprises a difussing screen.

3. The apparatus of claim 1, wherein a Fresnel lens is disposed on said casing at the level of said window aperture.

4. The apparatus of claim 2, wherein said diffusing screen is coupled through a pivoted rod to a lever rigid with the output shaft of a drive motor.

5. The apparatus of claim 1, wherein said unitary illuminating and projecting means is located with a twenty-degree inclination of said optical axis connecting said light source to said mirror in relation to the vertical.

6. The apparatus of claim 1, wherein the wall of said casing in which said window aperture is cut is inclined by about sixty degrees to the horizontal.

7. The ophthalmological apparatus of claim 1, wherein said mirror is secured to the centre of a strap pivotally mounted in a frame about a horizontal shaft, said frame being provided with a control drive member coupled through a pair of arms and a pivoted rod to said strap, said frame being rotatably mounted in turn to an end of said control drive member.

8. The apparatus of claim 7, wherein said shaft of said control drive member is set at an angle of 20 degrees to the vertical.

9. The apparatus of claim 1 wherein said dome has formed through its wall a fixation control orifice for enabling an operator to check the position of a patient's eye.

10. The apparatus of claim 9, wherein the lower edge of said screen forms an angle of 70 degrees to the axis connecting the position of patient's eye to said fixation control orifice.

11. The apparatus of claim 9, wherein the lateral limits of said screen forms an angle of 80 degrees to the axis connecting the patient's eye to said fixation control orifice.

12. The apparatus of claim 9, wherein the upper limit of said screen forms an angle of 60 degrees to the axis connecting the patient's eye to the fixation control orifice.

13. The apparatus of claim 1, wherein the patient's eye is positioned symmetrically to the position of said mirror in relation to the centre of said dome.

14. The apparatus of claim 9, wherein said screen has two different fixation points, namely one for each eye, which are aligned and shifted on either side of said fixation control orifice by an angle of 15 degrees to the centre of said dome.

* * * * *